United States Patent [19]

Morse et al.

[11] Patent Number: 5,333,626

[45] Date of Patent: Aug. 2, 1994

[54] PREPARATION OF BONE FOR TRANSPLANTATION

[75] Inventors: Brenda S. Morse, Chamblee, Ga.; Edward Shanbrom, Santa Ana, Calif.

[73] Assignee: Cryolife, Inc., Marietta, Ga.

[21] Appl. No.: 815,394

[22] Filed: Dec. 31, 1991

[51] Int. Cl.$^5$ ............................................. A61B 19/00
[52] U.S. Cl. ...................................... 128/898; 623/16; 422/27
[58] Field of Search .................. 604/48, 49; 600/36; 128/898; 424/78.25, 529; 435/1, 2, 268, 283; 422/28, 37, 29, 26, 27; 623/16, 18, 19, 20

[56] References Cited

U.S. PATENT DOCUMENTS

| | | | |
|---|---|---|---|
| 4,169,123 | 9/1979 | Moore et al. | 422/29 |
| 4,526,751 | 7/1985 | Gartner | 424/78.25 |
| 4,923,677 | 5/1990 | Simon et al. | 422/37 |
| 4,946,792 | 8/1990 | O'Leary | 435/268 |

FOREIGN PATENT DOCUMENTS 0964545  7/1964  United Kingdom .

OTHER PUBLICATIONS

Webster's New World Dictionary, 3rd Edition, pp. 260, 356 (1988).

*Primary Examiner*—C. Fred Rosenbaum
*Assistant Examiner*—V. Alexander
*Attorney, Agent, or Firm*—Kenyon & Kenyon

[57] ABSTRACT

The invention provides a simple, safe and effective method for treating bone and making it suitable for transplantation comprising: (a) contacting said bone with a global decontaminating agent effective to inactivate bacteria, fungi, virus and parasites; (b) cleaning said bone; and (c) terminally decontaminating said cleaned bone by contacting it with a global decontaminating agent effective to inactivate bacteria, fungi, virus and parasites. The invention also provides a method of cleaning bone which can be used in step (b) of the method described above and comprises contacting the bone with detergent under high pressure washing conditions at elevated temperatures.

45 Claims, 1 Drawing Sheet

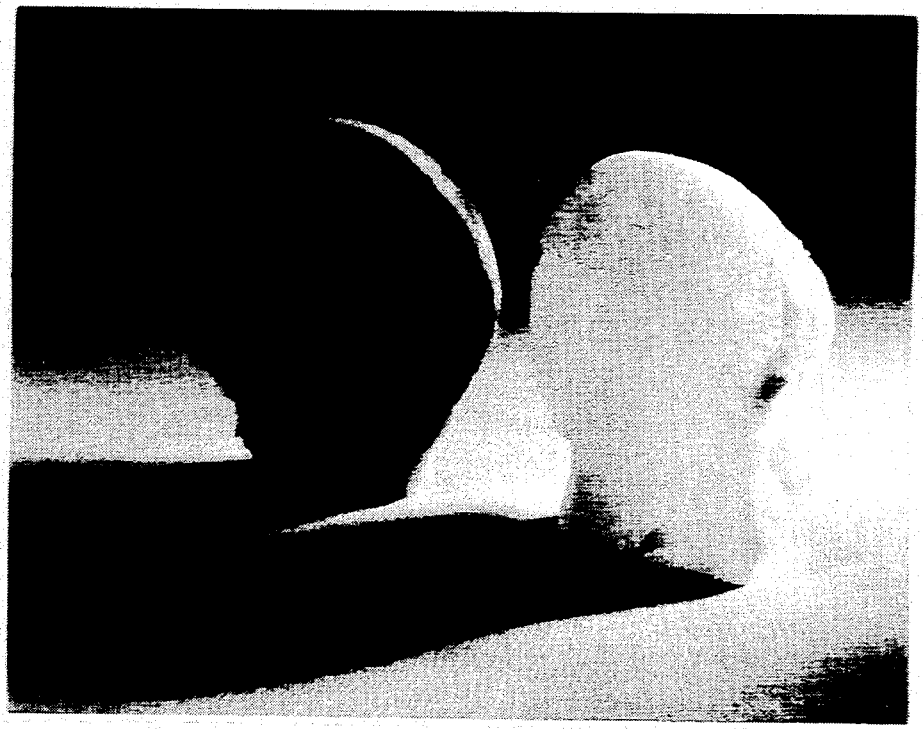

PREPARATION OF BONE FOR TRANSPLANTATION

FIELD OF THE INVENTION

The present invention relates to a method of processing bone for eventual transplantation. The method of the invention offers a simple, safe and effective way to produce clean, decontaminated bone for transplantation. It comprises contacting the bone with a global decontaminating agent effective to inactivate a wide range of infectious agents including bacteria, viruses, fungi and parasites; cleaning the bone; and terminally decontaminating the bone with a global decontaminating agent effective to inactivate a wide range of infectious agents including bacteria, viruses, fungi and parasites. The invention also offers an effective method of cleaning bone comprising contacting bone with detergent under high pressure washing conditions and elevated temperatures.

BACKGROUND OF THE INVENTION

The procurement and processing of human bone for transplantation has not changed significantly since the 1950s. It remains a complicated task which requires the coordinated efforts of several groups including the donor's family, the hospital staff, the local procurement group, the blood specimen processing laboratory, the bone processing laboratory, the transplant patient, and the transplant team.

A prime consideration is minimization of the risk of transferring potentially harmful diseases to tissue recipients. Viruses and bacteria can be transmitted by the bone as well as the marrow. See Kakaiya et al., "Tissue transplant-transmitted infections," Transfusion 31 (3) 1277–284, 1991; Shutkin, "Homologous-serum hepatitis following use of refrigerated bonebank bones, report of a case," J. Bone Joint Surg. 36 -A160, 1954. Transmission of human im nodeficiency virus (HIV) via bone as well as bone marrow has also been reported. "Transmission of HIV through bone transplantation case report and public health recommendations" Novbid. Mortal Weekly Rep., 37:597–599, 1988. Furlini et al., "Antibody response to human immunodeficiency virus after infected bone marrow transplant," Eur. J. Clin. Microbiol. Infect Dis, 7(5)554–665, 1988. Furthermore, HIV has been cultured from fresh as well as refrigerated bone and freeze-dried bone. Buck et al. "Human immunodeficiency virus cultured from bone. Implications for transplantation." Clin. Ortho., 251:249–253, 1990. Protection of the bone processing laboratory technician is another consideration which has become more pressing in recent years because of the possibility of HIV and hepatitis B transmission.

Current bone procurement and processing procedures have been designed to minimize these risks. Typically, the hospital and a local procurement agency first review hospital records regarding the potential donor's serology and disease status to determine if the donor falls within acceptable medical criteria. If all is in order and the required consents have been obtained, technicians from the local procurement agency begin collecting blood samples and removing specified organs, tissues and bones within hours of the donor's death. During the procurement process, the bones may be dipped in an antibiotic cocktail (usually a bacitracin/polymixin solution). Typically, the bones are then chilled on ice or frozen, and shipped to a processing laboratory.

At the processing laboratory the blood samples may be analyzed for a variety of known infectious agents including:
Human immunodeficiency virus (HIV-1)
Human immunodeficiency virus (HIV-2)
Human T cell lymphotropic virus (HTLV-1)
Hepatitis B
Hepatitis C
Cytomegalic virus (CMV)
*Treponema pallidum* (syphilis).

Typically, technicians proceed to thaw the bone and place the pieces in antibiotic cocktail. They then clean the bones with sterile water. After debridement of external fat and tissue with sterile water, the bones may be cut into specific sizes. Technicians remove the marrow using sterile water to which hydrogen peroxide may have been added to further defat and whiten the bone. Finally, if desired, the bone may be incubated in ethanol for at least one hour. Select bone pieces are packaged in such a way as to preserve sterility and biologic potential. A popular and practical method with processing laboratories is to lyophilize the bone to dryness, size, and package the select bone pieces. Other methods include cryopreservation and fresh freezing. To ensure sterility at the end of the process, samples from the packages are cultured for microorganisms.

The combination of donor screening and antibiotic treatments currently employed during processing reduces the risk of transmission of known vital contaminants and a variety of bacteria. Current methods however offer no prophylactic protection from viruses, select bacteria, and fungi which are common flora in humans and in a hospital environment. First, screening tests are not foolproof. Although the sensitivity and specificity of screening tests are high, false negatives may result from, for example, low antibody or antigen levels (e.g., recent infection or immunodeficiency) or even technician error. Furthermore screening tests may be useful only to identify known infectious agents. Second, antibiotic cocktails currently in use do not readily kill all types of bacteria. For example, the polymixin/bacitracin solution commonly used does not inactivate Proteus species. Furthermore, antibiotic cocktails have no significant effect on viruses or fungi.

While cleanliness of the bone is believed to be an important factor in avoiding transplant-related infection and antigenicity, it is difficult to clean bone pieces effectively by the conventional methods. Cells and debris harbor infectious agents and may provoke antigenic response.

The present invention provides a method of processing bone for transplantation having prophylactic protection from a wide range of infectious agents which are not readily inactivated or screened for by current methods. In particular, the present invention offers a simple method of not only decontaminating bone from a wide range of infectious agents, but also of effectively cleaning the bone so as to eliminate any cells or debris which may harbor such infectious agents.

The present invention also provides a method for cleaning and decontaminating human bone for transplantation which is safe for the laboratory technician.

These and other objects, features and advantages of the invention will become apparent after review of the following detailed description of the disclosed embodiments and the appended claims.

SUMMARY OF THE INVENTION

In accordance with the invention there is provided a simple, safe and effective method for treating bone and making it suitable for transplantation comprising:

a) contacting said bone with a global decontaminating agent effective to inactivate bacteria, fungi, virus and parasites;

b) cleaning said bone; and c) terminally decontaminating said cleaned bone by contacting it with a global decontaminating agent effective to inactivate bacteria, fungi, virus and parasites.

The invention also provides a method of cleaning bone which can be used in step (b) of the method described above and comprises contacting the bone with detergent under high pressure washing conditions at elevated temperatures.

SUMMARY OF THE FIGURES

In illustrating the invention, reference is made to FIG. 1 which is a photograph comparing femoral heads cleaned as described in Example 5. The femoral head on the left was cleaned by standard methods while that on the right was cleaned according to the high pressure/elevated temperature detergent cleaning method. The femoral heads were split to reveal the thoroughness of the cleaning process of the invention.

DETAILED DESCRIPTION OF THE INVENTION

For purposes of this disclosure, the term "bone" is used in the most general sense and includes all types of human or animal bone tissue, including whole bones, bone pieces, bone blocks with attached connective tissues such as ligaments and tendons, as well as ground bone preparations and ground demineralized bone preparations.

Initial or primary decontamination is accomplished by contacting the bone with a global decontaminating agent effective to inactivate bacteria, virus, fungi and parasites.

Contact time should be sufficient to effectively inactivate infectious agents. Preferably the bone is soaked in the global decontaminating solution for at least 2 or more minutes, preferably 10 or more minutes and most preferably at least one or more hours. During this primary decontaminating soaking, the bone may be removed from the solution for debridement of gross outer tissue and fat and then returned to the solution for further soaking.

The global decontaminating agent should be effective to inactivate bacteria, virus, fungi and parasites. Preferable decontaminating agents are the iodophors. Useful iodophors are polyvinyl pyrrolidone-iodine (PVP-I or povidone iodine) preparations available commercially from the Purdue-Frederick Company, ISP, formerly GAF, and BASF. Preferred PVP-I preparations are those of molecular weight less than 20,000 such as PVP-Iodine 17/12 of BASF. Of these, most preferred are those PVP-I preparations having molecular weights less than about 10,000. Suitable iodophor solutions may alternatively be prepared by mixing together a solution of the complexing agent (polyvinyl pyrrolidone in the case of PVP-I) having the desired molecular weight and molecular iodine in amounts sufficient to give the desired available iodine concentration. For example, an available iodine concentration of about 1% by weight may be obtained by dissolving 100 g of PVP in water, then with stirring adding 10 g of iodine, and finally adding sufficient water to bring the total volume to 1 liter. Other ratios of PVP to iodine may be used to obtain a PVP-I solution having the desired available iodine. Suitable available iodine concentrations are 0.03 to 1% by weight of Iodine to solution, preferably 0.1% to 0.5%.

Other decontaminating agents which have been found to inactivate a wide range of infectious agents including bacteria, fungi, parasites and virus are hydrogen peroxide, ethanol, ozone, ethylene oxide, irradiation and mixtures thereof and with PVP-I.

The global decontaminating agent solution should be of a concentration effective to inactivate bacteria, virus, fungi and parasites. Iodophor, concentration of the primary decontaminating solution is preferably in the range of 0.5 to 10% and most preferably 1 to 5% by weight with an available iodine concentration of 0.05 to 1%, preferably 0.1 to 0.5% by weight. PVP-I concentration is preferably in the range of 0.5 to 10% and most preferably 1 to 5% by weight of PVP-I, with an available iodine concentration of 0.05 to 1%, preferably 0.1 to 0.5% by weight.

The primary decontaminating solution may include a detergent, preferably in a concentration of 0.1 to 5% of the solution and most preferably 1 to 3% by weight or volume. Anionic, cationic, amphoteric and nonionic detergents are suitable. Preferable detergents are nonionic detergents like the polyethoxyethylene ethers (for example those marketed under the registered trademark Triton of Rhom & Haas by Union Carbide) or the polyoxyethylene sorbitan fatty acid esters (Tween series marketed by ICI and Sigma among others). Most preferably the detergent is octylphenoxypolyethoxyethanol (Triton X-100 TM Rhom & Haas). Of the polyoxyethylene sorbitans, polyoxyethylene (20) sorbitan monooleate (Tween 80) is most preferable.

Most advantageously, primary decontamination is effected by soaking the bone in 0.1 to 5% PVP-I, 1% (by volume) Triton X-100 TM solution for at least 2 or more minutes, preferably 10 or more minutes and most preferably at least one or more hours.

As Example 1 shows, the preliminary decontamination step of the invention is more effective than the prior art antibiotic cocktail. PVP-I is the preferred decontaminating agent due to its rapid action, the wide spectrum of infectious agents which it can inactivate (virus as well as bacteria, fungi and parasites) and its relatively low toxicity to human tissue. Furthermore, PVP-I has been found to inactivate HIV. The preliminary decontamination step not only protects the bone recipient by significantly reducing the risk of infection from the bone, but also protects laboratory technicians. The primary decontaminating solution, whether containing PVP-I or PVP-I and detergent furthermore renders the bone easier to clean by initially loosening or softening soft tissue, lipids, and blood products.

Cleaning after primary decontamination may be effected by conventional methods but is preferably effected by contacting bone with a detergent in such a way as to remove fat, marrow and other debris. The detergent lyses cells (e.g., blood cells) dissolves fat, and solubilizes proteins which comprise the bone marrow. The cleaning procedure may include agitation and/or elevated temperatures. Agitation could be effected by a gyratory shaker, vigorous agitation being most preferable. Such washing produces bone which has negligible marrow, cells, fat and debris and thus adds an additional margin of safety for the transplant recipient by removing cells which may harbor infectious agents.

Suitable, preferable and most preferable detergents are the same as those described above for the primary decontamination step. Detergent concentration is about 0.1% to 5% preferably about 1 to 3% by weight or volume. Preferably iodophor is added to the detergent solution in a concentration of 0.1 to 10%. Most preferably the iodophor is polyvinylpyrrolidone iodine.

Most advantageously, the bone is cleaned with a detergent solution under high pressure washing conditions at elevated temperatures. High pressure washing conditions should provide a force sufficient to drive the cleaning solution into internal matrix of the bone. Such high pressure washing conditions include, for example, vigorous agitation, such as with a paint can shaker, or high pressure lavage such as with a high pressure liquid jet stream. Suitable paint can shakers are those manufactured by Red Devil, preferably model # 0-5400-0M (615 rpm and 0.25 horsepower). The pressure of the liquid jet stream is preferably 100 to 3,000 psi and most preferably 500 to 1,500 psi. Most preferably the liquid jet stream is sterile and includes detergent. Cleaning is accelerated significantly and is more thorough if effected at temperatures within the range of 0° to 80° C., preferably 37° to 80° C. most preferably. High pressure washing effectively loosens marrow and progressively removes debris within the cancellous bone matrix. Following this high pressure washing procedure the bone is strikingly cleaner and whiter than bone processed by standard methods (See FIGS. 1).

To expedite cleaning the solution may be changed, for example by transferring the bone to fresh solution, during the cleaning operation. Preferably the solution is changed at least two times. After cleaning, detergent may be finally removed by repeated washing with sterile water. A biologically acceptable alcohol such as ethanol may also be used to remove the detergent. If an alcohol is used, it must be removed by rinsing with sterile water.

If bone blocks with attached connective tissue are to be cleaned, the connective—tissue tendons, ligaments, menisci, for example—should be covered with a sterile covering such as plastic wrap or sterile drape during the cleaning procedure.

The bone may be cleaned and decontaminated further by exposing it to hydrogen peroxide, which also has bactericidal properties. After washing with detergent, the bone is transferred to a 0.5 to 10%, preferably 3%, hydrogen peroxide solution for a time sufficient to allow for additional whitening and removal of trace fat. Agitation may be applied. Incubation time is suitably 5 to 120 minutes, preferably 5 to 60 minutes, and most preferably 15 to 30 minutes. After the treatment, residual peroxide is removed by extensive washing with sterile water.

After cleaning the bone is finally decontaminated prior to packaging. This terminal decontamination is effected by contacting the bone with a global decontaminating agent for at least about 2 or more minutes, preferably at least about 10 or more minutes and most preferably 30 to 60 or more minutes. Suitable, preferable and most preferable global decontaminating agents and concentrations are as described above for initial decontamination.

When cartilage or connective tissue is present the decontaminating and cleaning solutions preferably contain sodium chloride, or another biologically acceptable salt, in an amount sufficient to prevent the PVP-I from concentrating in the cartilage or connective tissue. Preferably 0.01 to 0.75 M NaCl, and most preferably 0.15 M NaCl is used.

The global decontaminating agent used for terminal decontamination may be removed from the bone by washing with sterile water, or left on as a thin coat to further protect the bone against infectious agents. The thus coated bone may be lyophilized.

Most preferably a PVP-I coat is allowed to form. PVP-I solution adhering to the bone imparts a rich golden amber, which can serve as an indicator that the bone has been treated. If desired, the amber bone may be lyophilized directly, packaged, and stored at room temperature, preferably in amber jars. While various methods of lyophilizing tissue are known in the art, a process that has been found suitable for lyophilizing bone is freeze-drying for about 10 to 168 hours, preferably about 20 to 28 hours. Residual PVP-I on the lyophilized bones continues to offer protection until removed by washing or by the body fluids after implantation. Likewise, the bone may be coated with other suitable global decontaminating agents, PVP or mixtures thereof.

Alternatively, the residual global decontaminating agent may be removed by rinsing with sterile water or inactivated by chemical reaction. The originally off-white bone color may thus be restored. Iodophors may be chemically inactivated by adding a reducing agent such as sodium ascorbate or thiosulfate, to the soaking solution after the required soaking time has elapsed. The reducing solution should be of a molarity and amount sufficient to inactivate the remaining molecular iodine. For example, 50 to 100 microliters of 1 M sodium ascorbate solution should be sufficient to inactivate 10 mls of 1% PVP-I. This treatment turns the solution back from dark brown to a clear color and returns the bone to its natural color.

After the terminal decontamination step, the bone may be lyophilized or cryopreserved or fresh frozen for storage.

It should be appreciated by those skilled in the art that bone treated in the manner herein disclosed is suitable for all therapeutic uses for which bone, is required, for example bone transplants, maxillofacial surgery and dental surgery.

The following examples serve to illustrate and more particularly describe the invention but are not intended to limit the invention.

EXAMPLE 1

Step 1: Primary Decontamination

Human bone was harvested, cultured and found to be contaminated with a variety of bacteria and fungi including:

Staphylococcus species (coagulase negative)
Enterococcus species
*Candida albicans*
*Acinetobacter anitratus*
*Klebiella pneumoniae.*

The ilium was soaked in a solution of 5% PVP-I (polyTinylpyrrolidone-Iodine, C15 complex from GAF). The gross outer tissue and fat was removed, the bone returned to 5% PVP-I for a total time of one (1) hour and the bone was tested (in five replicates) for residual contamination. The following table shows a comparison of the present method with incubations in saline, the positive control, and bacitracin/polymixin cocktail.

| Solution | Total Microorganisms/bone |
|---|---|
| Pre-treatment | 8,700 |
| Post-treatment | |
| Saline | 11,000 |
| Antibiotic cocktail | 4,300 |
| 5% PVP-I | 330 |

Results indicate the 5% PVP-I is superior to the antibiotic treatment in reducing the nun%her of infectious organisms. organisms.

Step 2: Cleaning

The bone was transferred to a screw top jar containing 1% (by volume) octylphenoxypolyethoxyethanol, (Triton X-100 TM at 37° C.) and shaken vigorously in a paint can shaker (Model No. 0-5400-OM manufactured by Red Devil) for 10 minutes. After transferring the bone to a clean solution of warm 1% Triton X-100 TM, the bone was incubated overnight (about 15 to 18 hours at 37–42° C.) and shaken vigorously for 10 minutes. The bone was transferred to fresh 1% Triton X-100 TM and again shaken vigorously for 10 minutes. Any remaining marrow was removed by lavage with sterile water.

Next, the bone was placed in 3% hydrogen peroxide, shaken for 10 minutes, and incubated for a total time of 60 minutes.

The cleaned bone was washed thoroughly with sterile water by lavage and repeated rinses until there was no evidence of detergent foam.

Step 3: Terminal Decontamination

The cleaned bone was placed in 1% PVP-I at room temperature, shaken vigorously for 10 minutes and incubated for a total time of 30 minutes, and removed from the solution.

Step 4: Storage

If desired, the PVP-I may be allowed to dry on the bone giving the bone a rich golden color and additional protection against infectire agents. The coated bone may then be lyophilized. Likewise, if desired, the bone may be coated with PVP by allowing PVP to dry on the bone.

EXAMPLE 2

Step 1. Primary decontamination

Human knee en bloc is harvested by the local procurement agency, packaged, and shipped on wet ice to a bone processing laboratory.

At the processing laboratory, the knee is placed into 1-5% PVP-I, 0.15M sodium chloride for 10 to 60 minutes.

Step 2. Tissue Preparation and Cleaning

The following knee tissues with adjoining bone blocks are removed:
*patella tendon*
*posterior cruciate ligament*
*anterior cruciate ligament*
*menisci*

The pieces are trimmed to remove excess tissue and fat. The ligament or tendon is wrapped in a sterile covering (e.g. plastic wrap or sterile drapes) while the bone blocks cleaned by lavage with warm (40–65° C.) 1% Triton X-100 TM followed by thorough rinsing with sterile water.

Step 3. Terminal Sterilization

The tissues are placed in 1% PVP-I, 0.15 M sodium chloride, gently shaken for 1 hour at room temperature, and rinsed thoroughly with sterile water. Each piece is cryopreserved, packaged, and stored in liquid nitrogen.

EXAMPLE 3

Step 1. Primary decontamination

Human diaphysial bones were harvested by the local procurement agency, packaged, and shipped on wet ice to a bone processing laboratory.

The processing laboratory placed the bones into 5% PVP-I, 1% Triton X-100 TM for 10 to 60 minutes.

Step 2. Tissue Preparation and Cleaning

The bones were debrided to remove excess tissue and fat, placed in 1% PVP - I, 1% Triton X- 100 TM. Next, the bones were further cleaned by lavage and incubation in warm (40–65° C.) 1% Triton X-100 TM followed by thorough rinsing with sterile water.

The bones were ground into chips in a bone mill, rinsed with sterile water, and lyophilized. The chips were ground to a finer size in a Tekrnar mill.

Step 3. Demineralization

The bone powder was demineralized with cold 0.6 N hydrochloric acid, and rinsed with sterile water.

Step 4. Terminal Sterilization

The demineralized powder was placed in 1% PVP-I for 1 hour, rinsed thoroughly with sterile water. The powder was transferred to vials, lyophilized, packaged, and stored at room temperature.

EXAMPLE 4

Terminal Sterilization With Inactivation of PVP-I

A bone, treated similarly to the bone of example 1, was placed in 20 mls of 1% PVP-I, and incubated for 1 hour. Following incubation, 0,132 mls of 0.91 sodium ascorbate were added. The solution almost immediately became clear and after 10 minutes the bone returned to its natural off-white color.

EXAMPLE 5

This example compares results obtained by the high pressure/elevated temperature detergent cleaning method with those obtained by standard methods. After cleaning the femoral heads were split to better show the degree the cleaning.

The femoral head shown on the right was incubated at 60° C. in 1% (by volume) Tween 80 for 2 days with periodic 10 minute agitations using a paint can shaker (Model No. 0-5400-0M manufactured by Red Devil). The femoral head was then lavaged with warm water, incubated in 3% hydrogen peroxide for 20 minutes, and then again lavaged with warm water to remove the hydrogen peroxide.

The femoral head shown on the left was cleaned according to standard methods. It was lavaged with 60° C. water for 15 minutes; incubated in 3% hydrogen peroxide for 15-20 minutes; again lavaged with 60° C. water to remove the hydrogen peroxide; incubated in 70% ethanol for 1 hour; and again lavaged with 60° C.

water to remove the ethanol. FIG. 2 is a photograph of the thus cleaned bone.

What is claimed is:

1. A method of providing bone suitable for transplantation into a human comprising the step of contacting, under a high pressure washing condition, the internal matrix of said bone with a solution comprising a decontaminating agent or a detergent.

2. A method according to claim 1 wherein said high pressure washing condition comprises lavage with a high pressure liquid stream.

3. The method of claim 2 wherein said high pressure liquid jet stream is at about 100 to 300 psi.

4. The method of claim 2 wherein said high pressure liquid jet stream is at about 500 to 1,500 psi.

5. The method of claim 2 wherein said liquid is a detergent.

6. A method according to claim 1 wherein said high pressure washing condition comprises vigorous agitation.

7. A method according to claim 1 wherein said high pressure washing thereof is conducted at a temperature between about 37 and 80° C.

8. Bone suitable for transplantation into a human produced according to the method of claim 1.

9. The method of claim 1 wherein said bone is further terminally decontaminated by contacting it with a global decontaminating agent effective to inactivate bacteria, fungi, virus and parasites.

10. The method of claim 1 wherein said cleaning is conducted at elevated temperatures.

11. The method of claim 10 wherein said elevated temperatures range from about 37° to 80° C.

12. The method of claim 10 wherein said elevated temperatures range from about 37° to 60° C.

13. The method of claim 1 wherein said detergent is a non-ionic detergent.

14. The method of claim 13 wherein said non-ionic detergent is octylphenoxypolyethoxyethanol.

15. The method of claim 13 wherein said non-ionic detergent is polyoxyethylene (20) sorbitan monooleate.

16. The method of claim 1 wherein the bone is additionally contacted with hydrogen peroxide.

17. A method of providing bone suitable for transplantation into a human comprising the step of contacting, under a high pressure washing condition, the internal matrix of said bone with a solution comprising a decontaminating agent or a detergent, said method comprising also an additional step of contacting said bone, prior to subjecting said internal matrix thereof to a high pressure washing condition, with a decontaminating agent having the capability to inactivate bacteria, fungi, virus, or parasites, said method further comprising an additional step of contacting, subsequent to said high pressure washing condition, said bone and said internal matrix thereof with a decontaminating agent also having said aforementioned capability.

18. Bone suitable for transplantation into a human produced according to the method of claim 17.

19. The method of claim 17 wherein said high pressure washing conditions include vigorous agitation, sufficient to drive said detergent into internal matrices of the bone.

20. The method of claim 17 wherein said high pressure washing conditions include contacting said bone with a high pressure liquid jet stream.

21. The method of claim 20 wherein said high pressure liquid jet stream is at about 100 to 3000 psi.

22. The method of claim 20 wherein said high pressure liquid jet stream is at about 500 to 1,500 psi.

23. The method of claim 20 wherein said liquid is a detergent.

24. The method of claim 17 wherein said cleaning is conducted at elevated temperatures.

25. The method of claim 24 wherein said elevated temperatures range from about 37° to 80° C.

26. The method of claim 24 wherein said elevated temperatures range from about 37° to 60° C.

27. The method of claim 17 wherein said detergent is a non-ionic detergent.

28. The method of claim 27 wherein said non-ionic detergent is octylphenoxypolyethoxyethanol.

29. The method of claim 17 wherein the bone is additionally contacted with hydrogen peroxide.

30. A method of preparing bone for transplantation into a human, said bone containing an internal matrix having a predetermined amount of marrow, blood cells, or fat, or of debris therefrom, comprising contacting said internal matrix with a solution, itself comprising a decontaminating agent or a detergent, and maintaining said solution under high pressure in contact with said matrix for a time effective to reduce said amount of marrow, cells, or fat, or of debris therefrom below said predetermined value thereof.

31. A method of preparing bone for transplantation into a human, said bone containing internal matrix having a predetermined amount of marrow, blood cells, or fat, or of debris therefrom at a predetermined pressure, said method comprising the step of subjecting said matrix to pressure different from said predetermined value, and then maintaining said matrix in contact therewith for a time effective to reduce said amount of marrow, cells, or fat, or of debris therefrom below said predetermined value thereof.

32. A method of preparing bone for transplantation into a human, said bone containing internal matrix having a predetermined amount of marrow, blood cells, or fat, or of debris therefrom at a predetermined pressure, said method comprising the steps of contacting said matrix with a solution comprising a decontaminating agent or a detergent at pressure different from said predetermined value, and then maintaining said matrix in contact therewith for a time effective to reduce said amount of marrow, cells, or fat, or of debris therefrom below said predetermined value thereof.

33. A method of providing bone suitable for transplantation into a human comprising the step of contacting, under a high pressure washing condition, the internal matrix of said bone with a solution comprising a decontaminating agent or a detergent, said high pressure washing condition including vigorous agitation sufficient to drive said decontaminating agent or detergent into internal matrices of the bone, said method comprising also an additional step of contacting said bone, prior to subjecting said internal matrix thereof to said high pressure washing condition, with a decontaminating agent having the capability to inactivate bacteria, fungi, virus, or parasites, said method further comprising an additional step of contacting, subsequent to said high pressure washing condition, said bone and said internal matrix thereof with a decontaminating agent also having said aforementioned capability.

34. A method of providing bone suitable for transplantation into a human comprising the step of contacting, under a high pressure washing condition, the internal matrix of said bone with a solution comprising a decontaminating agent or a detergent, wherein said high pressure washing condition comprising vigorous agitation.

35. A method of preparing bone suitable for transplantation into a human comprising the step of contacting, at an elevated temperature and under a high pressure washing condition, internal matrix of said bone with a solution comprising a decontaminating agent or a detergent, said high pressure washing condition being sufficient to drive said decontaminating agent or detergent into internal matrix of the bone.

36. A method according to 35 comprising also an additional step of contacting said bone, prior to subjecting said internal matrix thereof to said high pressure washing condition, with a decontaminating agent having the capability to inactivate bacteria, fungi, virus, or parasites.

37. A method according to claim 35 comprising also an additional step of contacting, subsequent to said high pressure washing condition, said bone and said internal matrix thereof with a decontaminating agent having the capability to inactivate bacteria, fungi, virus, or parasites.

38. A method according to claim 35 comprising also an additional step of contacting said bone, prior to subjecting said internal matrix thereof to said high pressure washing condition, with a decontaminating agent having the capability to inactivate bacteria, fungi, virus, or parasites, said method further comprising an additional step of contacting, subsequent to said high pressure washing condition, said bone and said internal matrix thereof with a decontaminating agent also having said aforementioned capability.

39. A method according to claim 35 wherein said high pressure washing condition comprises vigorous agitation.

40. A method according to claim 35 wherein said elevated temperature facilitates inactivation of virus.

41. A method according to claim 35 wherein said elevated temperature facilitates removal of fat from said internal matrix.

42. A method according to claim 35 wherein said bone utilized therein contains internal matrix having a predetermined amount of marrow, blood cells, or fat, or of debris therefrom, at a predetermined pressure, said method comprising the steps of first subjecting said matrix at an elevated temperature to pressure different from said predetermined value thereof, and then maintaining said matrix in contact with said pressure at said temperature of a time effective to reduce said amount of marrow, cells, or fat, or of debris therefrom below said predetermined value thereof.

43. A method according to claim 35 wherein, said bone utilized therein contains internal matrix having a predetermined amount of marrow, blood cells, or fat, or of debris therefrom, at a predetermined pressure, said method comprising the steps of contacting, at an elevated temperature and at a pressure above said predetermined value thereof, said matrix with a solution comprising a decontaminating agent or a detergent, and then maintaining said matrix in contact therewith, under said conditions of temperature and pressure, for a time effective to reduce said amount of marrow, cells, or fat, or of debris therefrom below said predetermined value thereof.

44. A method according to claim 35 wherein said high pressure washing is conducted at a temperature between about 37 and 80° C.

45. A method according to claim 35 wherein said high pressure washing is conducted at a temperature between about 37 and 60° C.

* * * * *

UNITED STATES PATENT AND TRADEMARK OFFICE
CERTIFICATE OF CORRECTION

PATENT NO. : 5,333,626         Page 1 of 3

DATED : August 2, 1994

INVENTOR(S) : Morse et al.

It is certified that error appears in the above-indentified patent and that said Letters Patent is hereby corrected as shown below:

Column 1, Line 40, delete "im nodeficiency" and insert --immunodeficiency-- therefor.
        Line 68, delete "polyrnixin" and insert --polymixin-- therefor.

Column 5, Line 26, delete "C." and insert --C.,-- therefor.
        Line 26, after "preferably", insert --37° to 60°C.--.
        Line 42, after "connective", insert --tissue--.

Column 6, Line 63, delete "polyTinylpyrrolidone-Iodine" and insert --polyvinylpyrrolidone iodine-- therefor.

Column 7, Line 1, delete "polyrnixin" and insert --polymixin-- therefor.
        Line 14, delete "nun%her" and insert --number-- therefor.
        Line 15, delete second occurrence of "organisms.".
        Line 44, delete "infectire" and insert --infective-- therefor.

UNITED STATES PATENT AND TRADEMARK OFFICE
CERTIFICATE OF CORRECTION

PATENT NO. : 5,333,626
DATED : August 2, 1994
INVENTOR(S) : Morse et al.

It is certified that error appears in the above-indentified patent and that said Letters Patent is hereby corrected as shown below:

Column 8, Line 27, delete "Tekrnar" and insert --Tekmar-- therefor.
Line 54, delete "the" and insert --of-- therefor.

Column 9, Line 13, delete "300" and insert --3000-- therefor.

Column 11, Line 2, delete "comprising" and insert --comprises-- therefor.

Column 12, Line 14, delete "of" and insert --for-- therefor.
Line 35, after "60°C.", insert the following claims:

--46. The method of claim 2, 3, 4, 5, 6, 17 or 30 wherein said decontaminating agent used therein is an iodophor.

UNITED STATES PATENT AND TRADEMARK OFFICE
CERTIFICATE OF CORRECTION

PATENT NO. : 5,333,626
DATED : August 2, 1994
INVENTOR(S) : Morse et al.

It is certified that error appears in the above-indentified patent and that said Letters Patent is hereby corrected as shown below:

47. The method of claim 46 wherein said decontaminating agent is polyvinylpyrrolidone iodine.

48. The method of claim 2, 3, 4, 5, 6, 17 or 30 wherein said bone is a bone block with attached connective tissue.

49. The method of claim 2, 3, 4, 5, 6, 17 or 30 wherein said bone is ground, or ground and demineralized, before terminal decontamination.--

Signed and Sealed this

Ninth Day of May, 1995

Attest:

BRUCE LEHMAN

Attesting Officer

Commissioner of Patents and Trademarks